(12) United States Patent
Vale et al.

(10) Patent No.: US 11,103,264 B2
(45) Date of Patent: *Aug. 31, 2021

(54) DEVICES AND METHODS FOR REMOVAL OF ACUTE BLOCKAGES FROM BLOOD VESSELS

(71) Applicant: NEURAVI LIMITED, Galway (IE)

(72) Inventors: David Vale, Barna (IE); Eamon Brady, Loughrea (IE); Michael Gilvarry, Headford (IE); David Hardiman, Raheny (IE); Brendan Casey, Barna (IE)

(73) Assignee: NEURAVI LIMITED, Galway (IE)

( * ) Notice: Subject to any disclaimer, the term of this patent is extended or adjusted under 35 U.S.C. 154(b) by 175 days.

This patent is subject to a terminal disclaimer.

(21) Appl. No.: 16/248,539

(22) Filed: Jan. 15, 2019

(65) Prior Publication Data

US 2019/0142442 A1    May 16, 2019

Related U.S. Application Data

(63) Continuation of application No. 14/207,069, filed on Mar. 12, 2014, now Pat. No. 10,201,360.
(Continued)

(51) Int. Cl.
*A61B 17/221* (2006.01)
*A61L 31/02* (2006.01)
(Continued)

(52) U.S. Cl.
CPC .......... *A61B 17/221* (2013.01); *A61L 31/022* (2013.01); *B05D 1/322* (2013.01);
(Continued)

(58) Field of Classification Search
CPC ........ A61B 17/22031; A61B 17/22032; A61B 17/221; A61B 17/32056;
(Continued)

(56) References Cited

U.S. PATENT DOCUMENTS 2,828,147 A    3/1958 Peiffer
3,361,460 A    1/1968 Jansen
(Continued)

FOREIGN PATENT DOCUMENTS

CN    2557083 Y    6/2003
CN    101172051 A    5/2008
(Continued)

OTHER PUBLICATIONS

US 6,348,062 B1, 02/2002, Hopkins (withdrawn)
(Continued)

*Primary Examiner* — Wade Miles
*Assistant Examiner* — Kankindi Rwego
(74) *Attorney, Agent, or Firm* — Troutman Pepper Hamilton Sanders LLP

(57) ABSTRACT

A clot retrieval device with an elongate shaft and an expandable section, the expandable section having a framework of interconnected strut elements distal of the elongate shaft, the strut elements forming an outer expandable body and an inner expandable body. At least a portion of the strut elements include a first coating of radiopaque material defining a plurality of micro-columns, wherein each micro-column includes a length extending between a first end coupled to one of the plurality of strut elements and a second free end opposite the first end, the length of each micro-column is longer than a width of each micro-column. The second free end is capable of moving further apart when a convex bend is applied to the respective strut element during use. Also including a second coating.

13 Claims, 12 Drawing Sheets

Related U.S. Application Data

(60) Provisional application No. 61/784,940, filed on Mar. 14, 2013.

(51) Int. Cl.
  *B05D 1/32* (2006.01)
  *B05D 3/12* (2006.01)
  *A61B 17/00* (2006.01)
  *A61B 17/22* (2006.01)
  *A61B 90/00* (2016.01)

(52) U.S. Cl.
  CPC ...... *B05D 3/12* (2013.01); *A61B 2017/00526* (2013.01); *A61B 2017/00867* (2013.01); *A61B 2017/00942* (2013.01); *A61B 2017/00951* (2013.01); *A61B 2017/2212* (2013.01); *A61B 2017/2217* (2013.01); *A61B 2017/22034* (2013.01); *A61B 2090/3966* (2016.02)

(58) Field of Classification Search
  CPC ........... A61B 2017/00526; A61B 2017/00867; A61B 2017/00942; A61B 2017/22034; A61B 2017/22035; A61B 2017/2212; A61B 2017/2215; A61B 2017/2217; A61B 90/39; A61B 2090/3966; A61B 2017/00951; A61L 31/022; A61L 31/08; A61L 31/082; A61L 31/084; A61L 31/086; A61L 31/088; A61L 31/10; C23C 30/00; A61F 2/01; A61F 2/013; A61F 2002/011; A61F 2002/015; A61F 2002/016; A61F 2002/018; B05D 1/322; B05D 3/12
  USPC ........................................................ 606/200
  See application file for complete search history.

(56) References Cited

U.S. PATENT DOCUMENTS

| | | |
|---|---|---|
| 4,455,717 A | 6/1984 | Gray |
| 4,612,931 A | 9/1986 | Dormia |
| 4,793,348 A | 12/1988 | Palmaz |
| 4,873,978 A | 10/1989 | Ginburg |
| 5,011,488 A | 4/1991 | Ginsburg |
| 5,084,065 A | 1/1992 | Weldon et al. |
| 5,092,839 A | 3/1992 | Kipperman |
| 5,102,415 A | 4/1992 | Guenther et al. |
| 5,122,136 A | 6/1992 | Guglielmi et al. |
| 5,163,951 A | 11/1992 | Pinchuk et al. |
| 5,171,233 A | 12/1992 | Amplatz |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,387,219 A | 2/1995 | Rappe |
| 5,387,226 A | 2/1995 | Miraki |
| 5,449,372 A | 9/1995 | Schmaltz |
| 5,499,985 A | 3/1996 | Hein et al. |
| 5,538,512 A | 7/1996 | Zenzon et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark |
| 5,769,871 A | 6/1998 | Mers Kelly |
| 5,769,884 A | 6/1998 | Solovay |
| 5,779,716 A | 7/1998 | Cano |
| 5,810,874 A | 9/1998 | Lefebvre |
| 5,814,064 A | 9/1998 | Daniel et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,702 A | 6/1999 | Romley et al. |
| 5,911,725 A | 6/1999 | Boury |
| 5,919,126 A * | 7/1999 | Armini .................. A61F 2/82 600/3 |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,099,559 A | 8/2000 | Nolting |
| 6,102,932 A | 8/2000 | Kurtz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,231,597 B1 | 5/2001 | Deem et al. |
| 6,238,412 B1 | 5/2001 | Dubrul |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,488,701 B1 | 12/2002 | Nolting et al. |
| 6,511,492 B1 | 1/2003 | Rosenbluth |

(56) References Cited

U.S. PATENT DOCUMENTS

| | | |
|---|---|---|
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack |
| 6,602,265 B2 | 8/2003 | Dubrul et al. |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson |
| 6,726,703 B2 | 4/2004 | Broome et al. |
| 6,730,104 B1 | 5/2004 | Sepetka |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukemik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B1 | 3/2007 | Takayanagi et al. |
| 7,220,271 B2 | 5/2007 | Clubb |
| 7,226,464 B2 | 6/2007 | Garner et al. |
| 7,229,472 B2 | 6/2007 | DePalma et al. |
| 7,288,112 B2 | 10/2007 | Denardo et al. |
| 7,300,458 B2 | 11/2007 | Henkes et al. |
| 7,306,618 B2 | 12/2007 | Demond |
| 7,314,483 B2 | 1/2008 | Landau et al. |
| 7,316,692 B2 | 1/2008 | Huffmaster |
| 7,323,001 B2 | 1/2008 | Clubb |
| 7,331,976 B2 | 2/2008 | Vale |
| 7,344,550 B2 | 3/2008 | Carrison et al. |
| 7,399,308 B2 | 7/2008 | Borillo et al. |
| 7,410,491 B2 | 8/2008 | Hopkins |
| 7,425,215 B2 | 9/2008 | Boyle et al. |
| 7,452,496 B2 | 11/2008 | Brady et al. |
| 7,491,215 B2 | 2/2009 | Vale |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin, Jr. |
| 7,604,650 B2 | 10/2009 | Bergheim |
| 7,609,649 B1 | 10/2009 | Bhandari et al. |
| 7,618,434 B2 | 11/2009 | Santra |
| 7,662,165 B2 | 2/2010 | Gilson et al. |
| 7,670,356 B2 | 3/2010 | Mazzocchi |
| 7,678,123 B2 | 3/2010 | Chanduszko |
| 7,691,121 B2 | 4/2010 | Rosenbluth |
| 7,691,124 B2 | 4/2010 | Balgobin |
| 7,708,770 B2 | 5/2010 | Linder |
| 7,717,929 B2 | 5/2010 | Fallman |
| 7,736,385 B2 | 6/2010 | Agnew |
| 7,758,606 B2 | 7/2010 | Streeter et al. |
| 7,758,611 B2 | 7/2010 | Kato |
| 7,766,934 B2 | 8/2010 | Pal |
| 7,771,452 B2 | 8/2010 | Pal |
| 7,780,694 B2 | 8/2010 | Palmer |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Mazzocchi |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson |
| 8,187,298 B2 | 5/2012 | Pal |
| 8,246,641 B2 | 8/2012 | Osborne et al. |
| 8,246,672 B2 | 8/2012 | Osborne et al. |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,287,538 B2 | 10/2012 | Brenzel et al. |
| 8,298,257 B2 | 10/2012 | Sepetka et al. |

(56) References Cited

U.S. PATENT DOCUMENTS

| | | |
|---|---|---|
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandield et al. |
| 8,574,262 B2 | 11/2013 | Ferrera et al. |
| 8,574,915 B2 | 11/2013 | Zhang et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,919 B2 | 7/2014 | Kimura et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolick et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,173,688 B2 | 11/2015 | Dosta |
| 9,186,487 B2 | 11/2015 | Dubrul |
| 9,198,687 B2 | 12/2015 | Fulkerson et al. |
| 9,204,887 B2 | 12/2015 | Cully |
| 9,211,132 B2 | 12/2015 | Bowman |
| 9,221,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,898 B2 | 5/2017 | Palepu et al. |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 9,939,361 B2 | 4/2018 | Gajji et al. |
| 10,070,878 B2 | 9/2018 | Ma |
| 10,201,360 B2 * | 2/2019 | Vale .................. B05D 3/12 |
| 10,376,274 B2 | 8/2019 | Farin et al. |
| 10,390,850 B2 | 8/2019 | Vale et al. |
| 2001/0001315 A1 | 5/2001 | Bates |
| 2001/0016755 A1 | 8/2001 | Addis |
| 2001/0037141 A1 | 11/2001 | Yee et al. |
| 2001/0037171 A1 | 11/2001 | Sato |
| 2001/0049554 A1 | 12/2001 | Ruiz et al. |
| 2001/0051810 A1 | 12/2001 | Dubrul |
| 2002/0004667 A1 | 1/2002 | Adams et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |

(56) References Cited

U.S. PATENT DOCUMENTS

| | | |
|---|---|---|
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest |
| 2003/0004540 A1 | 1/2003 | Linder et al. |
| 2003/0004542 A1 | 1/2003 | Wensel |
| 2003/0009146 A1 | 1/2003 | Muni |
| 2003/0009191 A1 | 1/2003 | Wensel |
| 2003/0038447 A1 | 2/2003 | Cantele |
| 2003/0040772 A1 | 2/2003 | Hyodoh et al. |
| 2003/0050663 A1 | 3/2003 | Khachin |
| 2003/0064151 A1 | 4/2003 | Klinedinst |
| 2003/0108224 A1 | 6/2003 | Ike |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153158 A1 | 8/2003 | White |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0208224 A1 | 11/2003 | Broome |
| 2003/0212430 A1 | 11/2003 | Bose |
| 2003/0236533 A1 | 12/2003 | Wilson |
| 2004/0064179 A1 | 4/2004 | Linder et al. |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland |
| 2004/0133232 A1 | 7/2004 | Rosenbluth et al. |
| 2004/0138692 A1 | 7/2004 | Phung |
| 2004/0153118 A1 | 8/2004 | Clubb |
| 2004/0215318 A1 | 10/2004 | Kwitkin |
| 2005/0033248 A1 | 2/2005 | Sepetka |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0058837 A1 | 3/2005 | Farnworth et al. |
| 2005/0059995 A1 | 3/2005 | Sepetka |
| 2005/0085849 A1 | 4/2005 | Sepetka |
| 2005/0090779 A1 | 4/2005 | Osypka |
| 2005/0090857 A1 | 4/2005 | Kusleika et al. |
| 2005/0125024 A1 | 6/2005 | Sepetka |
| 2005/0149997 A1 | 7/2005 | Wolozin et al. |
| 2005/0171566 A1 | 8/2005 | Kannemura |
| 2005/0173135 A1 | 8/2005 | Almen |
| 2005/0192627 A1 | 9/2005 | Whisenant et al. |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0288686 A1 | 12/2005 | Sepetka |
| 2006/0008332 A1 | 1/2006 | Greenberg et al. |
| 2006/0009798 A1 | 1/2006 | Callister et al. |
| 2006/0009799 A1 | 1/2006 | Kleshinski et al. |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088383 A1 | 4/2007 | Pal et al. |
| 2007/0149997 A1 | 6/2007 | Muller |
| 2007/0156170 A1 | 7/2007 | Hancock |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0225749 A1 | 9/2007 | Martin |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097386 A1 | 4/2008 | Osypka |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0178890 A1 | 7/2008 | Townsend et al. |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188887 A1 | 8/2008 | Batiste |
| 2008/0200946 A1 | 8/2008 | Braun |
| 2008/0200947 A1 | 8/2008 | Kusleika et al. |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel |

(56) References Cited

U.S. PATENT DOCUMENTS

| | | |
|---|---|---|
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson |
| 2009/0105737 A1 | 4/2009 | Fulkerson |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lazier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0292297 A1 | 11/2009 | Ferrere |
| 2009/0292307 A1 | 11/2009 | Razack |
| 2009/0299393 A1 | 12/2009 | Martin |
| 2009/0299403 A1 | 12/2009 | Chanduszko et al. |
| 2009/0306702 A1 | 12/2009 | Miloslavski |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnett et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0022149 A1 | 1/2011 | Cox et al. |
| 2011/0054504 A1 | 3/2011 | Porter |
| 2011/0054514 A1 | 3/2011 | Arcand |
| 2011/0054516 A1 | 3/2011 | Keegan |
| 2011/0060212 A1 | 3/2011 | Slee et al. |
| 2011/0060359 A1 | 3/2011 | Hannes |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0276120 A1 | 11/2011 | Gilson et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0123466 A1 | 5/2012 | Porter et al. |
| 2012/0143237 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0271788 A1 | 10/2013 | Garrison |
| 2013/0281788 A1 | 10/2013 | Garrison |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0180397 A1 | 6/2014 | Gerberding et al. |
| 2014/0183077 A1 | 7/2014 | Rosendall et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0372779 A1 | 12/2014 | Wong et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0112376 A1 | 4/2015 | Molaei et al. |
| 2015/0133990 A1 | 5/2015 | Davidson |
| 2015/0164523 A1 | 6/2015 | Brady et al. |
| 2015/0250497 A1 | 9/2015 | Marks et al. |
| 2015/0257775 A1 | 9/2015 | Gilvarry et al. |
| 2015/0297252 A1 | 10/2015 | Miloslayski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022269 A1 | 1/2016 | Ganske et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0317168 A1 | 11/2016 | Brady et al. |
| 2017/0007264 A1 | 1/2017 | Cruise et al. |
| 2017/0007265 A1 | 1/2017 | Guo et al. |

(56) References Cited

U.S. PATENT DOCUMENTS

| | | |
|---|---|---|
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2019/0167284 A1 | 6/2019 | Friedman et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |

FOREIGN PATENT DOCUMENTS

| | | |
|---|---|---|
| CN | 102307613 A | 1/2012 |
| CN | 102596098 A | 7/2012 |
| CN | 104042304 A | 9/2014 |
| CN | 105662532 A | 6/2016 |
| CN | 205359559 U | 7/2016 |
| DE | 202009001951 U1 | 4/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| EP | 2301450 A1 | 3/2011 |
| EP | 301450 B1 | 11/2011 |
| EP | 2438891 A1 | 4/2012 |
| EP | 2628455 A1 | 2/2013 |
| GB | 2494820 A | 3/2013 |
| JP | 0919438 A | 1/1997 |
| JP | H0919438 A | 1/1997 |
| JP | 2014511223 A | 5/2014 |
| WO | 94/24926 | 11/1994 |
| WO | 97/27808 | 8/1997 |
| WO | 97/38631 A1 | 10/1997 |
| WO | 99/20335 | 4/1999 |
| WO | 99/60933 | 12/1999 |
| WO | 99/56801 | 4/2000 |
| WO | 01/21077 | 3/2001 |
| WO | 02/02162 | 1/2002 |
| WO | 02/11627 | 2/2002 |
| WO | 02/43616 | 6/2002 |
| WO | 02/070061 | 9/2002 |
| WO | 02/094111 | 11/2002 |
| WO | 03/002006 | 1/2003 |
| WO | 03/030751 | 4/2003 |
| WO | 03/051448 | 6/2003 |
| WO | 2004/028571 A2 | 4/2004 |
| WO | 2004/056275 A1 | 7/2004 |
| WO | 2005/000130 A1 | 1/2005 |
| WO | 2005/027779 A2 | 3/2005 |
| WO | 2006/021407 | 3/2006 |
| WO | 2006/031410 | 3/2006 |
| WO | 2006/107641 | 10/2006 |
| WO | 2008/135823 A2 | 12/2006 |
| WO | 2006135823 A2 | 12/2006 |
| WO | 2007/054307 | 5/2007 |
| WO | 2007/068424 | 6/2007 |
| WO | 2008/034615 | 3/2008 |
| WO | 2008/051431 A1 | 5/2008 |
| WO | 2008/131116 | 10/2008 |
| WO | 2009031338 A1 | 3/2009 |
| WO | 2009/076482 | 6/2009 |
| WO | 2009/086482 | 7/2009 |
| WO | 2009/105710 A1 | 8/2009 |
| WO | 2010/010545 | 1/2010 |
| WO | 2010/046897 A1 | 4/2010 |
| WO | 2010/075565 A2 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/110316 A1 | 9/2011 |
| WO | 2011106426 A1 | 9/2011 |
| WO | 2012/052982 A1 | 4/2012 |
| WO | 2012/064726 A1 | 5/2012 |
| WO | 2012/081020 A1 | 6/2012 |
| WO | 2012/120490 A2 | 9/2012 |
| WO | 2012/110619 A1 | 10/2012 |

(56) References Cited

FOREIGN PATENT DOCUMENTS

| | | |
|---|---|---|
| WO | 2012156924 A1 | 11/2012 |
| WO | 2012/120490 A3 | 12/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2013187927 A1 | 12/2013 |
| WO | 2014047650 A1 | 3/2014 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | 2015/061365 A1 | 4/2015 |
| WO | 2015103547 A1 | 7/2015 |
| WO | 2015/134625 A1 | 9/2015 |
| WO | 2015/179324 A2 | 11/2015 |
| WO | 2015189354 A1 | 12/2015 |
| WO | 2016/010995 A1 | 1/2016 |
| WO | 2016089451 A1 | 6/2016 |
| WO | 2017089424 A1 | 6/2017 |

OTHER PUBLICATIONS

Extended European Search report issued in corresponding European Patent Application No. 19 15 1969 dated Oct. 29, 2019.
Partial European Search Report for Application No. 19151969.3 dated Jul. 12, 2019.
International Search Report for International Application No. PCT/IE2012/000011 dated Oct. 10 , 2012.
Written Opinion and International Search Report for International Application No. PCT/IE2011/000026 dated Jul. 27, 2011.
International Search Report for International Application No. PCT/IE2011/000057 dated Feb. 3, 2012.
Partial International Search Report for International Application No. PCT/EP2014/054828 dated Jun. 2, 2014.

\* cited by examiner

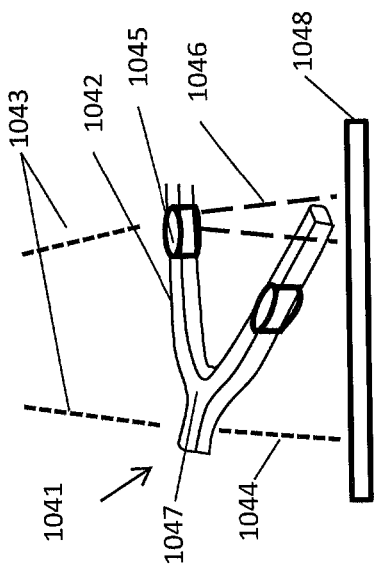
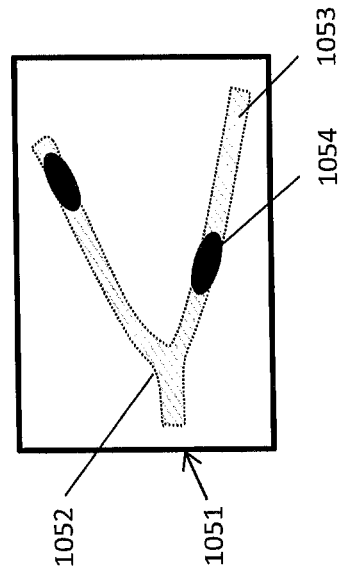
Fig 3a
Fig 3b
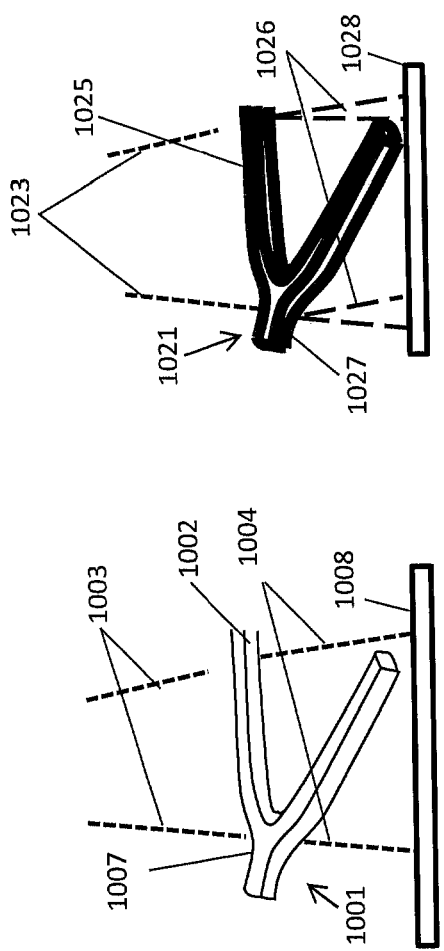
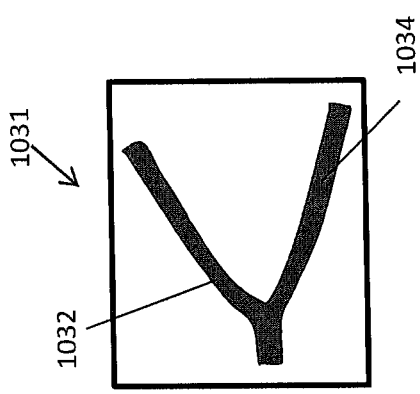
Fig 2c
Fig 2d
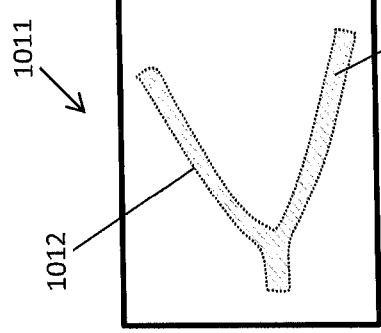
Fig 2a
Fig 2b

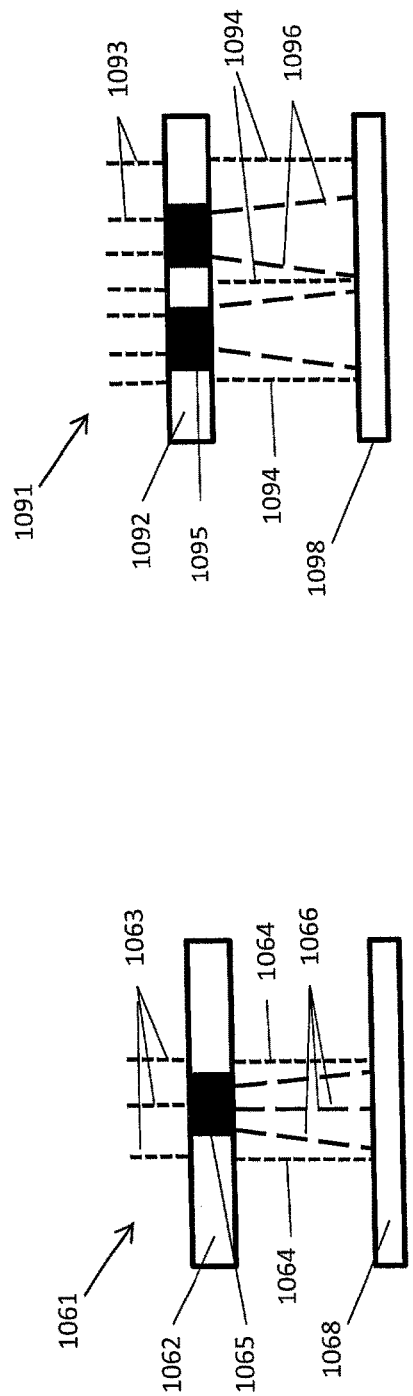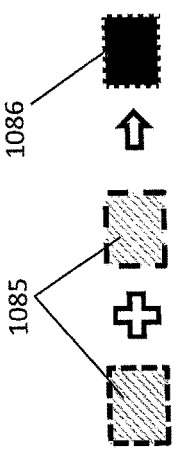

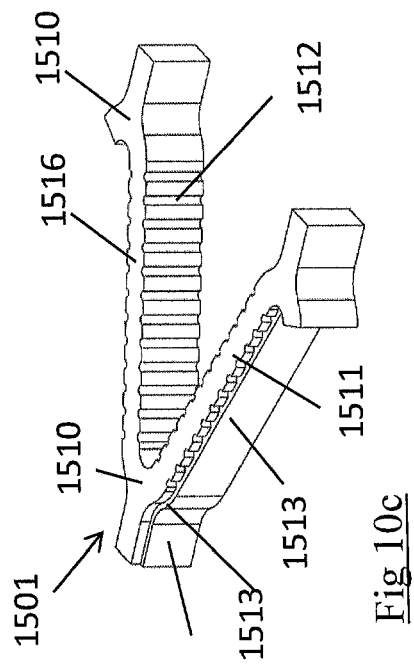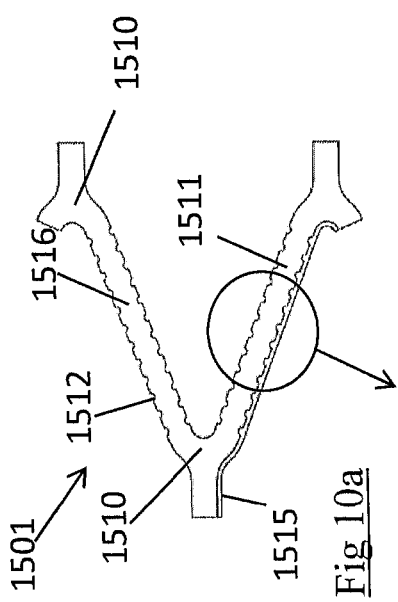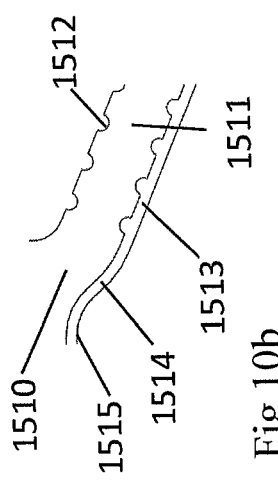

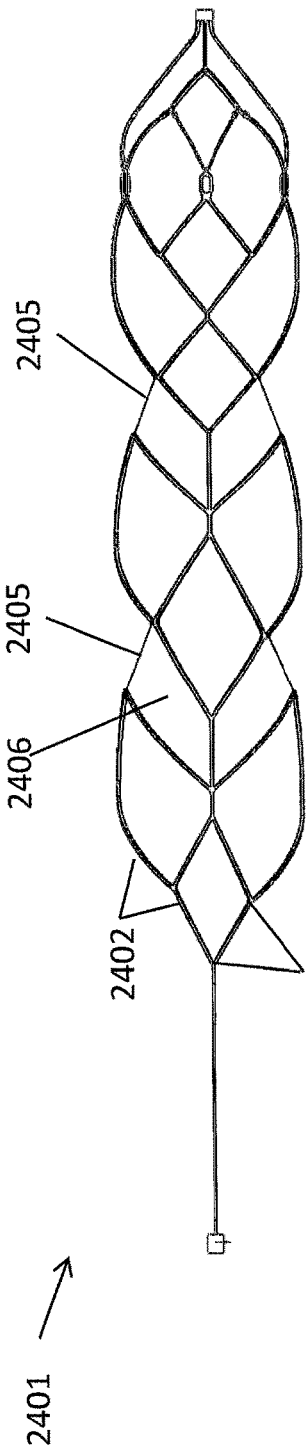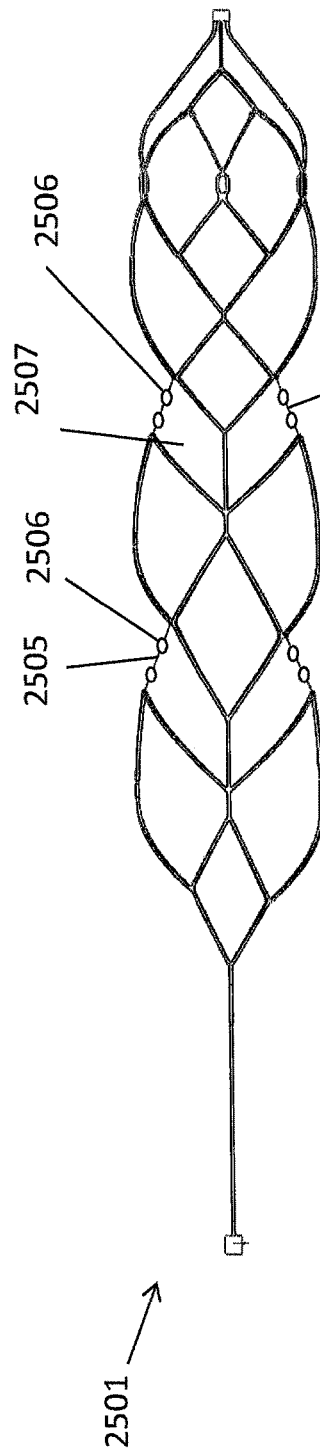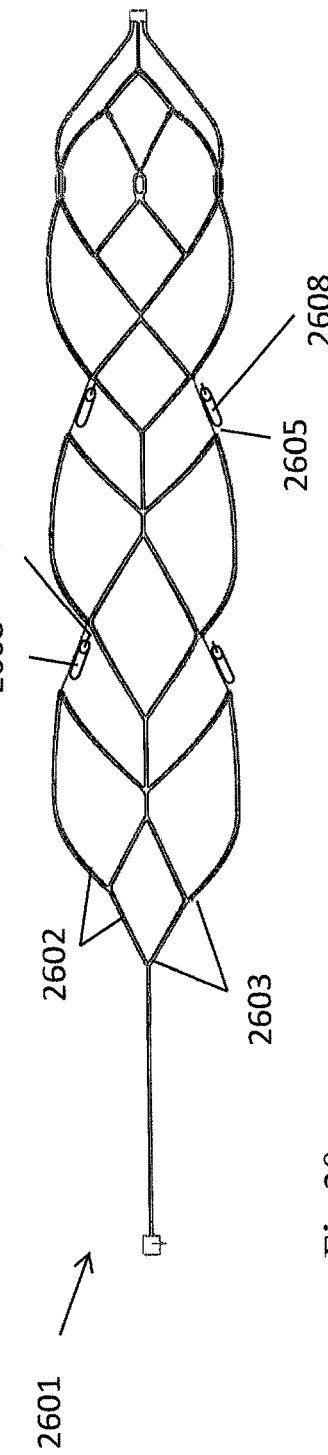

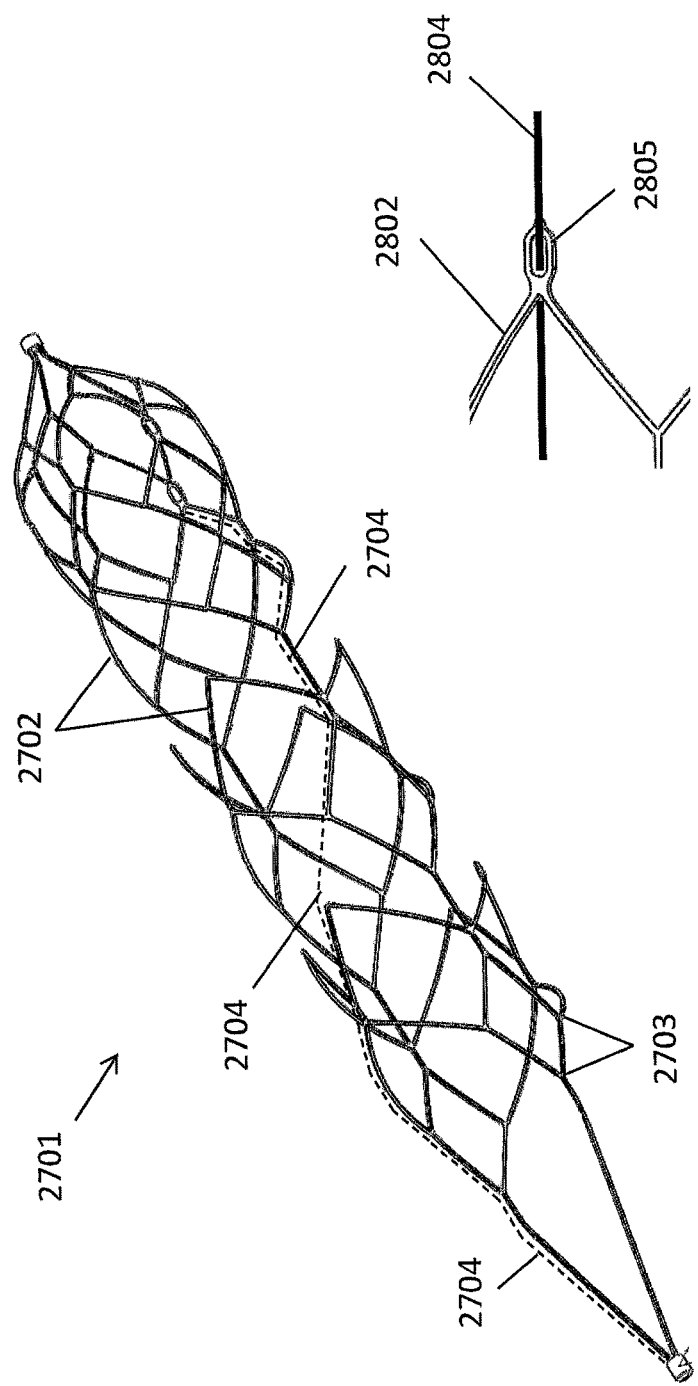
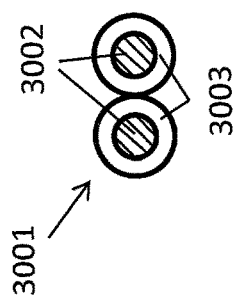
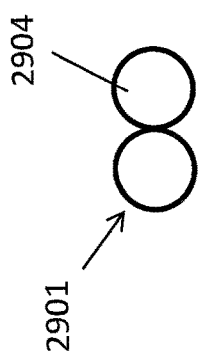

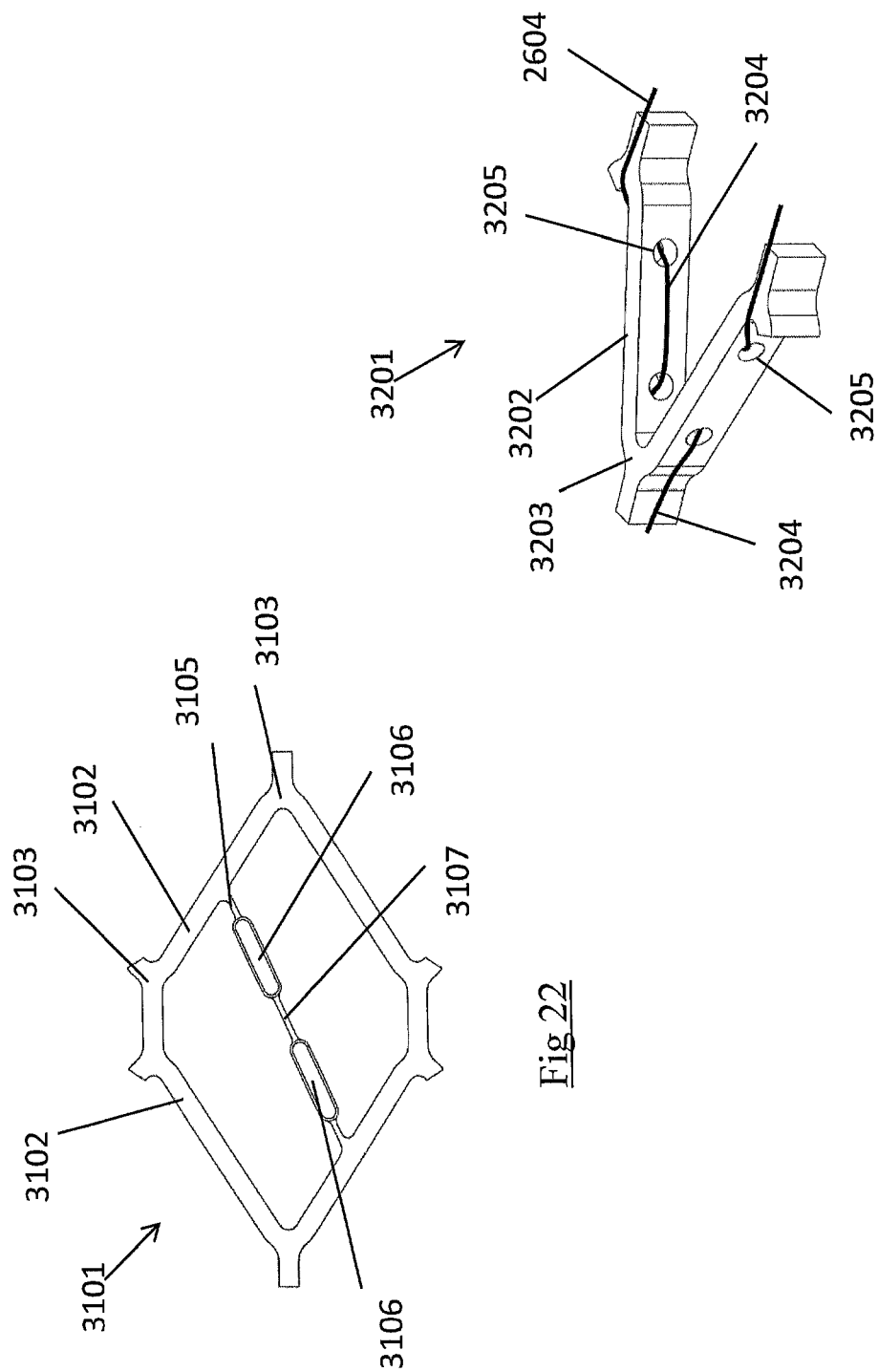

DEVICES AND METHODS FOR REMOVAL OF ACUTE BLOCKAGES FROM BLOOD VESSELS

CROSS-REFERENCE TO RELATED APPLICATION

This application is a continuation application of U.S. application Ser. No. 14/207,069, filed Mar. 12, 2014 which claims the benefit of U.S. Provisional Application No. 61/784,940, filed Mar. 14, 2013, each of which is incorporated herein by reference in their entirety.

FIELD OF THE INVENTION

This invention relates to devices intended for removing acute blockages from blood vessels. The invention especially relates to means of rendering such devices visible under xray or fluoroscopy. Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. The invention is particularly suited to removing clot from cerebral arteries in patients suffering acute ischemic stroke (AIS), from coronary native or graft vessels in patients suffering from myocardial infarction (MI), and from pulmonary arteries in patients suffering from pulmonary embolism (PE) and from other peripheral arterial and venous vessels in which clot is causing an occlusion.

BACKGROUND

Clot retrieval devices comprising a self-expanding Nitinol stent-like member disposed at the end of a long shaft are commonly used to remove clot from blood vessels, particularly from patients suffering from acute ischemic stroke. These devices are typically provided with small marker bands at either end of the self-expanding member which help to indicate the device's position. It would be very beneficial to a physician to be able to see the full expandable body of such a device under fluoroscopy, and thus receive visual information on the device's condition as rather than simply its position. Clot retrieval procedures are conducted under an x-ray field in order to allow the user visualize the anatomy and at a minimum the device position during a procedure. It is desirable, and enhances the user experience to be able to visualize the device state as well as position structure during a procedure, for example if the device is in an expanded configuration or a collapsed configuration. This means that the radiopaque sections must move closer to the device axis in a collapsed configuration and further from a device axis in an expanded configuration. It is generally desirable to make interventional devices such as clot retrieval devices more flexible and lower profile to improve deliverability in interventional procedures. This may be achieved by reducing the dimensions for device features, and the level of contrast seen under x-ray is generally reduced as the device dimensions are reduced. Radiopaque materials generally comprise noble metals such as gold, tantalum, tungsten, platinum, iridium and the like, and generally have poor elastic recovery from a strained condition and are therefore not optimal material for devices, particularly for the regions of these devices undergoing high strain in moving from a collapsed to an expanded state and vice versa. Radiopaque materials may be added through coating a structure comprising a highly recoverable elastic material such as Nitinol, but coating the entire structure has a dampening effect that inhibits device performance.

This invention overcomes limitations associated with the dampening effect of adding radiopaque material to an expandable clot retrieval device, while making the structure sufficiently radiopaque to allow full visualization of the device condition as well as position.

STATEMENT OF THE INVENTION

Various devices and method are described in our PCT/IE2012/000011 which was published under the number WO2012/120490A. This PCT application claims the benefit of U.S. Provisional 61/450,810, filed Mar. 9, 2011 and U.S. Provisional 61/552,130 filed Oct. 27, 2011. The corresponding U.S. National stage is U.S. application Ser. No. 13/823,060 filed on Mar. 13, 2013 and issued as U.S. Pat. No. 9,301,769, on Apr. 5, 2016. The entire contents of all of the above-listed applications are herein incorporated by reference. In addition, we hereby incorporate by reference in its entirety our U.S. Provisional Application No. 61/785,213 (Client Ref. 00007-0009-00600) entitled "A Clot Retrieval Device for Removing Occlusive Clot from a Blood Vessels" filed on Mar. 14, 2013.

This invention is particularly applicable to clot retrieval devices comprising expandable bodies made from a metallic framework. Such a framework might be a Nitinol framework of interconnected struts, formed by laser (or otherwise) cutting a tube or sheet of material, and may thus comprise a structure with a pattern of strut features and connector features. In some embodiments the clot retrieval device may comprise an inner expandable member and an outer expandable member, which may define a flow lumen through a clot and engage a clot.

In order to go from a collapsed to an expanded configuration, portions of the device undergo recoverable deformation and varying levels of strain. Some portions require a higher level of recoverable strain than others in order to work effectively. Where the framework or expandable member comprises a pattern of strut features and connector features, the struts typically comprise inflection regions or connection regions generally referred to as crowns, which typically experience higher strain than the struts or connectors when the device is collapsed or expanded.

The term detector is generally referred to as the part of the equipment which collects the beam for processing into useful images, and can include for example flat panel detectors or image intensifiers. X-ray beams are filtered through an anti-scatter grid during processing. This filters out scattered beams which deflect significantly from the trajectory of the source beam, and beams less significantly deflected off the original trajectory pass through the anti-scatter grid creating areas of overlap between non-scattered photon beams and scattered photon beams, referred to herein as shadow areas.

In an embodiment of this invention discrete markers are placed in low strain regions of the clot retrieval device members, and high strain regions comprise a super elastic material with little or no radiopaque material.

In use, it is desirable to maximize visibility and therefore maximize the area and volume of radiopaque markers located in the clot retrieval device. Increasing the ratio of radiopaque material to Nitinol generally improves radiopacity. For the effective operation of the device in moving between expanded and collapsed configurations, it is desirable to maintain a ratio of Nitinol to radiopaque material such that strain levels from an expanded to a collapsed configuration are substantially in the elastic region. This creates a conflict of requirements, and the solutions provided herein overcome this conflict.

Discrete markers placed in close proximity create overlapping shadow areas, referred to as intersection zones herein, which give the illusion under x-ray imaging of a continuous marker thereby providing fuller visual information to the user in an x-ray image.

Various embodiments of the invention are described in more detail below. Within these descriptions various terms for each portion of the devices may be interchangeably used. Each of the described embodiments are followed by a list of further qualifications (preceded by the word "wherein") to describe even more detailed versions of the preceding headline embodiment. It is intended that any of these qualifications may be combined with any of the headline embodiments, but to maintain clarity and conciseness not all of the possible permutations have been listed.

One embodiment of a device of this invention comprises a clot retrieval device comprising an elongate shaft and an expandable section, the expandable section comprising a framework of interconnected strut elements, the connection region between adjacent strut elements comprising crown elements, said framework formed from a substrate material, at least a portion of a plurality of said strut elements coated with a coating material, and at least a portion of a plurality of said crown elements not coated with said coating material.

Wherein the substrate material has a density of less than 10 g/cm$^3$.

Wherein the substrate material has a density of less than 8 g/cm$^3$.

Wherein the coating material has a density of more than 10 g/cm$^3$.

Wherein the coating material has a density of more than 15 g/cm$^3$.

Wherein the coating material has a density of more than 18 g/cm$^3$.

Wherein the substrate material is a superelastic material such as Nitinol or other super or pseudo elastic metallic alloy.

Wherein the coating material is Gold, Tantalum, Tungsten, Platinum or an alloy of one of these elements or other dense element or alloy containing one or more radiodense elements.

Wherein the coating material comprises a polymer or adhesive filled with a dense or high atomic number material such as Barium Sulphate, Bismuth SubCarbonate, Barium OxyChloride, Gold, Tungsten, Platinum or Tantalum.

Wherein the coating material is applied using an electroplating process, a dipping process, a plasma deposition process, an electrostatic process, a dip or spray coating process, a sputtering process, a soldering process, a cladding process or a drawing process.

Another aspect of this invention comprises a method of manufacturing the expandable body of a clot retrieval device, the expandable body comprising a substrate material and a coating material, the method comprising:

a first step of applying the coating material to the substrate material, a second step of removing at least a portion of said coating material from at least one area of said substrate material, and a third step of cutting away regions of both coating and substrate material to form an interconnected pattern of coated and uncoated regions.

Wherein the first step comprises an electroplating process, a dipping process, a plasma deposition process, an electrostatic process, a dip or spray coating process, a sputtering process, a soldering process, a cladding process or a drawing process.

Wherein the second step comprises a grinding process, a polishing process, a buffing process, an etching process, a laser cutting or laser ablation process.

Wherein the third step comprises a laser cutting process, a wire cutting process, a water jet cutting process, a machining process or an etching process.

Wherein the coating material is Gold, Tantalum, Tungsten, Platinum or an alloy of one of these elements or other dense element or alloy containing one or more radiodense elements.

Wherein the coating material comprises a polymer or adhesive filled with a dense or high atomic number material such as Barium Sulphate, Bismuth SubCarbonate, Barium OxyChloride, Gold, Tungsten, Platinum or Tantalum.

Wherein the substrate material comprises Nitinol, or an alloy of Nitinol or another super or pseudo elastic alloy.

Wherein the interconnected pattern comprises a plurality of strut elements and connector elements.

Wherein the interconnected pattern of the Clot Retrieval device comprises an expanded state and a collapsed state.

Wherein the second step removes at least a portion of the coating from those areas of the interconnected pattern which experience the highest strain in moving from the expanded state to the collapsed state, and/or from the collapsed state to the expanded state.

Wherein the strut elements terminate in crown elements,

Wherein the second step removes some or all of the coating from the crown elements.

Wherein the second step removes some or all of the coating from discrete sections of the strut elements; in one embodiment these discrete sections comprising stripes across the width of the struts.

Another embodiment of a device of this invention comprises a clot retrieval device comprising an elongate shaft and an expandable section, the expandable section formed from a substrate material, at least a portion of the substrate material coated with a first coating material and at least a portion of the first coating material coated with a second coating material;

Wherein the substrate material is a superelastic material such as Nitinol or other super or pseudo elastic metallic alloy.

Wherein the first coating material is Gold, Tantalum, Tungsten, Platinum or an alloy of one of these elements or other dense element or alloy containing one or more radiodense elements.

Wherein the first coating material is applied by a plasma deposition process, an electrostatic process, a dip or spray coating process, a sputtering process, a sputtering process using a cylindrical magnetron, a soldering process, a cladding process or a drawing process.

Wherein the first coating material comprises a porous or non-porous columnar structure.

Wherein the first coating material comprises a porous columnar structure, comprising generally independent columns of the coating material which extend substantially perpendicularly to the substrate surface.

Wherein said columns have a first end and a second end, said first end being adjacent the substrate surface, and the spacing between the second ends of adjacent columns varying with deformation of the substrate material/expandable body.

Wherein the second ends of the first coating material define an outer surface, and said outer surface is a rough surface.

Wherein the second coating material comprises a smooth surface, and/or a soft surface.

Wherein the second coating material is a polymeric material.

Wherein the elastic modulus of the second coating material is lower than that of the first coating material.

Wherein the elastic modulus of the second coating material is lower than that of the substrate material.

Wherein the elastic modulus of the second coating material is less than 50% of that of the first coating material and/or substrate material.

Wherein the elastic modulus of the second coating material is less than 40% of that of the first coating material and/or substrate material.

Wherein the elastic modulus of the second coating material is less than 30% of that of the first coating material and/or substrate material.

Wherein the elastic modulus of the second coating material is less than 20% of that of the first coating material and/or substrate material.

Wherein the elastic modulus of the second coating material is less than 10% of that of the first coating material and/or substrate material.

Wherein the second coating material is a hydrophilic material or a hydrogel.

Wherein the coefficient of friction of the first coating material is greater than 0.2.

Wherein the coefficient of friction of the first coating material is greater than 0.3.

Wherein the coefficient of friction of the first coating material is greater than 0.4.

Wherein the coefficient of friction of the first coating material is greater than 0.5.

Wherein the coefficient of friction of the second coating material is less than 0.2.

Wherein the coefficient of friction of the second coating material is less than 0.15.

Wherein the coefficient of friction of the second coating material is less than 0.1.

Wherein the coefficient of friction of the second coating material is less than 0.08.

Another embodiment of a device of this invention comprises a clot retrieval device comprising an elongate shaft and an expandable member, the expandable member comprising a proximal section, a body section and a distal section, the body section comprising a metallic framework of a first (or substrate) material, the metallic framework comprising a plurality of strut elements, said strut elements comprising an outer surface, an inner surface and side wall surfaces, at least one of said surfaces comprising a smooth surface and recessed features, at least some of said recessed features at least partially filled with a second coating material.

Wherein the recessed features comprise grooves or slots in the top surface of a strut element.

Wherein the recessed features comprise holes in the top surface of a strut element, Wherein the recessed features comprise holes through a strut element.

Wherein the above holes are circular, or oblong, or square or rectangular.

Wherein the recessed features comprise grooves or slots in the side wall of a strut element.

Wherein all of the recessed features are filled with the second coating material.

Wherein at least one of the smooth surfaces are coated with the second coating material.

Wherein all of the smooth surfaces are coated with the second coating material.

Wherein the thickness of coating material in the recessed features is greater than the thickness of coating material on the smooth surfaces.

Another aspect of this invention comprises a method of manufacturing the expandable body of a clot retrieval device, the expandable body comprising a substrate material and a coating material, the method comprising: a first step of removing material from discrete areas of the substrate material to form recesses, a second step of applying the coating material to the substrate material and recesses, and a third step of removing some or all of the coating from the non-recessed areas of the substrate.

Another aspect of this invention comprises a method of applying a radiopaque coating to selective areas of the expandable body of a clot retrieval device, the method involving a masking material and comprising:

a first step of applying a masking material to selective areas of the expandable body, a second step of applying a coating material to the expandable body, and a third step of removing the masking material from the expandable body.

Another aspect of this invention comprises a method of manufacturing the expandable body of a clot retrieval device, the expandable body comprising a substrate material and a coating material, the method involving a masking material and comprising:

a first step of applying the masking material to the substrate material, a second step of removing at least a portion of said masking material from at least one area of said substrate material, a third step of cutting away regions of both masking and substrate material to form an expandable body with masked and unmasked regions, a fourth step of applying a coating material to the expandable body, such that the coating material adheres to the unmasked areas but does not adhere to the masked areas of the expandable body, and a fifth step of removing the masking material from the expandable body.

Wherein the fourth step comprises an electroplating process, a dipping process, a plasma deposition process, an electrostatic process, a dip or spray coating process, a sputtering process, a soldering process, a cladding process or a drawing process.

Wherein the second step comprises a grinding process, a polishing process, a buffing process, an etching process, a laser cutting or laser ablation process.

Wherein the third step comprises a laser cutting process, a wire cutting process, a water jet cutting process, a machining process or an etching process.

Wherein the coating material is Gold, Tantalum, Tungsten, Platinum or an alloy of one of these elements or other dense element or alloy containing one or more radiodense elements.

Wherein the coating material comprises a polymer or adhesive filled with a dense or high atomic number material such as Barium Sulphate, Bismuth SubCarbonate, Barium OxyChloride, Gold, Tungsten, Platinum or Tantalum.

Wherein the substrate material comprises Nitinol, or an alloy of Nitinol or another super or pseudo elastic alloy.

Wherein the expandable body comprises a plurality of strut elements and connector elements.

Wherein the expandable body of the Clot Retrieval device comprises an expanded state and a collapsed state.

Wherein the third step results in the masking material being positioned on those areas of the expandable body which experience the highest strain in moving from the expanded state to the collapsed state, and/or from the collapsed state to the expanded state.

Another embodiment of a device of this invention comprises a clot retrieval device comprising an expandable body and an elongate shaft, the expandable body comprising a proximal section, a body section and a distal section, the body section comprising a framework of strut elements and at least one fiber assembly, the fiber assembly comprising a radiodense material.

Wherein the distal section comprises a clot capture scaffold.

Wherein the clot capture scaffold comprises a net.

Wherein the fiber assembly comprises at least one fiber and at least one floating element, the floating element comprising a radiodense material.

Wherein the fiber comprises a polymer monofilament, or plurality of polymer filaments.

Wherein the polymer filament is of LCP, Aramid, PEN, PET, or UEMWPE.

Wherein the fiber comprises at least one metallic filament.

Wherein the metallic filament is a nitinol wire, or plurality of such wires

Wherein the metallic filament comprises a nitinol outer layer with an inner core of a radiodense material such as Gold, Platinum, Tantalum or Tungsten.

Wherein the floating element is a coil, a tube, or a bead.

Wherein the material of the floating element comprises Gold, Tantalum, Tungsten, Platinum or an alloy of one of these elements or other dense element or alloy containing one or more radiodense elements.

Wherein the material of the floating element comprises a polymer filled with a dense and/or high atomic number material such as Barium Sulphate, Bismuth SubCarbonate, Barium OxyChloride or Tantalum.

BRIEF DESCRIPTION OF THE DRAWINGS

FIG. 2a is an isometric view of a portion of a clot retrieval device comprising standard material under x-ray imaging FIG. 2b is a representation of an x-ray image of FIG. 2a FIG. 2c is an isometric view of a portion of another clot retrieval device comprising a radiopaque material under x-ray imaging FIG. 2d is a representation of an x-ray image of FIG. 2c FIG. 3a is an isometric view of a portion of another clot retrieval device comprising standard material and radiopaque material under x-ray imaging FIG. 3b is a representation of an X-ray image FIG. 4a is a cross section view of a strut feature of a clot retrieval device comprising standard material and radiopaque material FIG. 4b is a representation of an x-ray image of FIG. 4a FIG. 5 schematically represents the resulting x-ray image from two adjacent shadow zones FIG. 6a is a cross section of a strut feature of a clot retrieval device comprising standard material and spaced apart radiopaque material features FIG. 6b is the a representation of an x-ray image from FIG. 6a FIG. 7a is an isometric view of a portion of a clot retrieval device FIG. 10a is a view of a portion of a clot retrieval device.

FIG. 10b is a detail view of a region of the device shown in FIG. 10a.

FIG. 10c is an isometric view of the device shown in FIG. 10a.

FIG. 20a is a side view of part of a clot retrieval device of this invention.

FIG. 20b is a side view of part of a clot retrieval device of this invention.

FIG. 20c is a side view of part of a clot retrieval device of this invention.

FIG. 21a is an isometric view of part of a clot retrieval device of this invention.

FIG. 21b is a detail view of a region of the device of FIG. 21a.

FIG. 21c is a section through one embodiment of a part of FIG. 21a.

FIG. 21d is a section through another embodiment of a part of FIG. 21a.

FIG. 22 is a view of a portion of a clot retrieval device of this invention.

FIG. 23 is an isometric view of part of a clot retrieval device of this invention.

DETAILED DESCRIPTION

Specific embodiments of the present invention are now described in detail with reference to the figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

The following detailed description is merely exemplary in nature and is not intended to limit the invention or the application and uses of the invention. Although the description of the invention is in the context of treatment of intracranial arteries, the invention may also be used in other body passageways as previously described.

Figure 1:
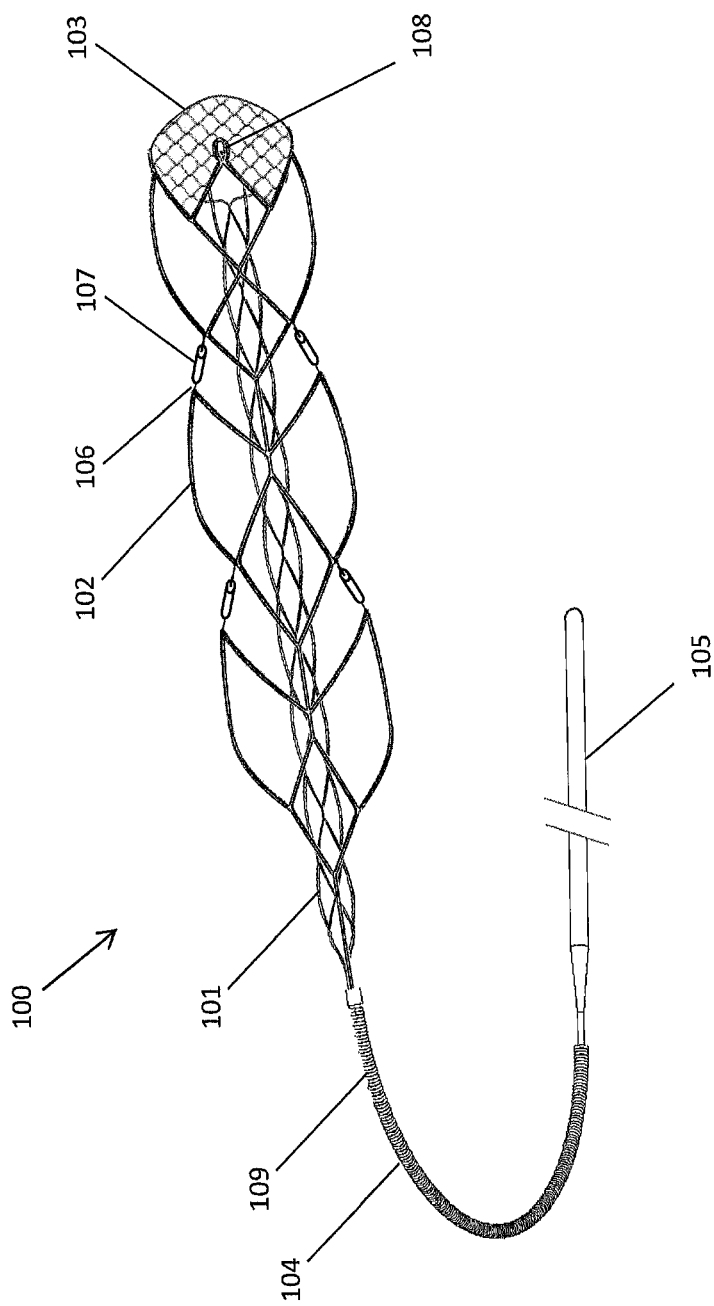
FIG. 1 is a side view of a clot retrieval device of this invention.

FIG. 1 is an isometric view of a clot retrieval device 100 with an inner expandable member 101 and outer member 102. In use, inner member 101 creates a flow channel through a clot and its freely expanded diameter is less than that of outer member 102. The inner and outer members are connected at their proximal ends to an elongate shaft 104, whose proximal end 105 extends outside of the patient in use. A distal fragment capture net 103 may be attached to the distal end of the device.

Positional visualization of this device may be provided by proximal Radiopaque coil 109 and distal radiopaque markers 108. User visualization of device 100 would be enhanced by providing visual information to the user on device expansion in a vessel or clot. This information may allow the user to visualize the profile of a clot and provide a fuller map of the luminal space created upon device deployment. As the device is withdrawn, the user will see the device response as it tracks through the anatomy with clot incorporated. It is therefore desirable to add radiopaque materials to outer member 102 and/or to inner tubular member 101 to provide the highest quality information to the user. One of the challenges with incorporating radiopaque material in such a manner is the dampening effect such materials have on superelastic Nitinol. The inventions disclosed in this document facilitate incorporation of radiopaque material and therefore product visualization without compromising the superelastic response of the outer member or inner tubular member. It is intended that any of the designs and inventions disclosed may be adopted to enhance the radiopacity of a clot retrieval device such as shown in FIG. 1, or any clot retrieval device comprising an expandable body.

In the embodiment shown the radiopacity of the outer member is enhanced by the presence of Radiopaque elements 107, which are attached to the outer member by supporting fibers 106. These fibers may be connected to the framework of the outer member by a variety of means, including threading the fibers through eyelets or attachment features. Radiopaque elements 107 may comprise tubes, beads or coils of a radiodense material such as Gold, Tungsten, Tantalum, Platinum or alloy containing these or other high atomic number elements. Polymer materials might also be employed, containing a Radiopaque filler such as Barium Sulphate, Bismuth SubCarbonate, Barium Oxy-Chloride or Tantalum.

FIG. 2a is an isometric view of a portion of a clot retrieval device 1001 with strut feature 1002 and crown feature 1007 comprising a superelastic material such as Nitinol. The portion of the clot retrieval device is shown is an expanded configuration. It can be appreciated that in the collapsed configuration, for clot retrieval device delivery, the struts 1002 may move to a position adjacent each other. During an interventional procedure, such as a neurothrombectomy procedure, the patient anatomy and device location in visualized with the aid of x-ray equipment such as a fluoroscope. Source x-ray beam 1003 originates at a photon beam source and targets device 1001. Partially scattered x-ray beam 1004 is the photon beam deflected by device 1001 which passes to detector 1008. Partially scattered x-ray beam generically refers to a photon beam which may be absorbed or scattered by a material (e.g. photoelectric absorption or Compton scattering). For materials, such as Nitinol that is relatively non-radiopaque relative to the treatment environment, source photon beams 1004 may pass through the device relatively uninterrupted, without being absorbed, changing trajectory, or without a significant wavelength change.

FIG. 2b is a representation of resulting image 1011 captured by detector 1008 in FIG. 2a. Low contrast image 1013 represents the outline of device 1012 under x-ray. Device 1012 may not be visible or barely visible if it is comprises standard material such as Nitinol and/or if device strut feature dimensions are small enough to be below a detectable range. This is due to the level of scattering of the x-ray or photon beam being relatively uninterrupted by device 1012 relative to the tissue environment in which it is placed.

FIG. 2c is an isometric view of a portion of a clot retrieval device 1021 with strut feature 1022 and crown feature 1027 comprising a radiopaque material, or a superelastic material such as Nitinol fully covered with radiopaque material through a process such as electroplating or sputtering. Source x-ray beam 1023 is a source photon beam between and x-ray source and device 1021. Highly scattered x-ray beam 1025 is the photon beam between device 1001 and detector 1008. As a source x-ray beam 1023 passes through radiopaque materials, such as noble metals such as gold, platinum, and the like, the level of scattering of a beam is relatively much greater than the level of scattering of either an adjacent non-radiopaque device comprising Nitinol or relative to the treatment environment where source x-ray beams 1023 pass through relatively uninterrupted.

FIG. 2d is a representation of resulting image 1031 captured by detector 1028 in FIG. 2c. High contrast image 1034 represents the outline of device 1032 under x-ray. Device 1032 is highly visible as it comprises a radiopaque material or material combination such as Nitinol coated with a radiopaque material. This is due to the difference high level of scattering of the x-ray or photon beam, highly uninterrupted by device 1032 relative to the tissue environment in which it is placed.

FIG. 3a is an isometric view of a portion of a clot retrieval device 1041 with strut feature 1042 and crown feature 1047. The device structure substantially comprises superelastic Nitinol material, especially at crown feature 1047 where a high level of elastic recovery is desirable for effective device operation. Discrete radiopaque marker 1045 is located on strut feature 1042 as an example of a location on a structural feature of the device which deflects less and requires less elastic recovery than other features of the device, for example crown feature 1047. Several embodiments of devices incorporating discrete radiopaque marker 1045 are disclosed later. Source x-ray beam 1043 is used to image device 1041 and in this example a mixture of highly scattered x-ray beam 1046 and partially scattered x-ray beam 1044 reach detector 1048.

FIG. 3b is a representation of x-ray image 1051 of device 1052 captured by detector 1048 (FIG. 3a). Low contrast image 1053 represents areas of device 1041 in FIG. 3a comprising superelastic materials such as Nitinol and high contrast image 1054 represents the location of discrete radiopaque marker 1045 in FIG. 3a which interrupts the path of x-ray source beam 1043. Device 1052 is partially visible to the user as it comprises sections of a radiopaque material and non-radiopaque material. This is due to the difference level of scattering of the x-ray or photon beam, highly uninterrupted by discrete radiopaque marker 1045 relative to the tissue environment and strut feature 1042 and crown feature 1047 comprising superelastic material such as Nitinol which has a partially scattered x-ray beam.

FIG. 4a and FIG. 4b further represent the scattering of x-ray beams and interruption of beam patterns as they pass through a medical device such as a clot retrieval device. FIG. 4a is a cross section view of clot retrieval device 1061 comprising strut feature 1062 with discrete radiopaque marker 1065. Source x-ray beam 1063 passes through the device, and the photon beam reaches x-ray detector 1068 to image device 1061. The wavelength and trajectory of partially scattered photon beam 1066 passed through strut feature 1062 comprising nitinol material without significant disruption. The wavelength and trajectory of highly scattered photon beam 1066 passed through discrete radiopaque marker 1065 is significantly changed or absorbed by said discrete radiopaque marker.

FIG. 4b is an illustration of x-ray image 1071 with low contrast image 1074, high contrast image 1073, and shadow zone 1075. Shadow zone 1075 in FIG. 4b occurs as a result of a mixture of partially scattered photon beams 1064 and highly scattered photon beams 1066 reaching the same area of detector 1068 in FIG. 4a.

FIG. 5 is a graphical representation of an x-ray image resulting from of two adjacent shadow zones 1085 combining to create Intersection Zone 1086.

FIG. 6a is a cross section view of a portion of a clot retrieval device 1091 with strut feature 1092 and a plurality of discrete radiopaque markers 1095. The device structure substantially comprises superelastic Nitinol material, especially strut feature 1092 and especially areas where a high level of elastic recovery is desirable for effective device operation such as crown features not shown in this drawing. A plurality of discrete radiopaque markers 1095 are located on strut feature 1092 as an example of a location on a structural feature of the device which deflects less and requires less elastic recovery than other features of the device. Source x-ray beam 1093 is used to image device 1091 and in this example a mixture of highly scattered x-ray beams 1096 and partially scattered x-ray beam 1094 reach detector 1098 after filtration through an anti-scatter grid.

FIG. 6b is a representation of x-ray image 1101 of device 1092 (FIG. 3a) captured by detector 1098 (FIG. 3a). Low contrast image 1104 represents areas of device 1091 in FIG. 3a comprising superelastic materials such as Nitinol and high contrast image 1104 represents the location of discrete radiopaque markers 1095 in FIG. 3a which interrupts the path of x-ray source beam 1043. Shadow Zone 1105 in FIG. 3a corresponds with, referring back to FIG. 3a, a location where a mixture of highly scattered x-ray beams 1096 and partially scattered x-ray beams 1094 reach the same location of x-ray detector 1098. Intersection Zone 1106 in FIG. 3b represents a zone where, referring back to FIG. 3a, a mixture of highly scattered x-ray beams 1096 and partially scattered x-ray beams 1094 reach the same location of x-ray detector 1098 in a region where discrete radiopaque markers 1095 are located in relatively close proximity. The configuration has the advantage of creating the illusion for the user of a continuous marker under x-ray imaging, thereby providing fuller information on the geometry of the device.

Figure 7A:
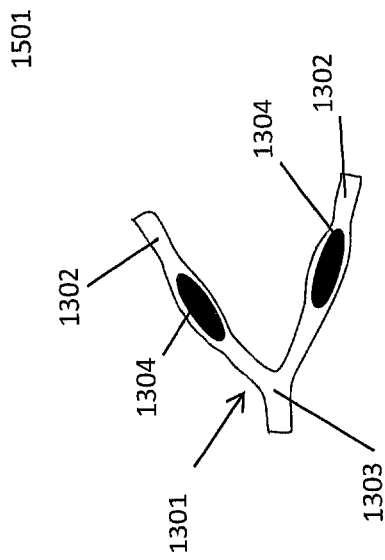
FIG. 7b is a developed plan view of the portion of a clot retrieval device from FIG. 7a FIG. 8 is a developed plan view of a portion of another clot retrieval device
Figure 7B:
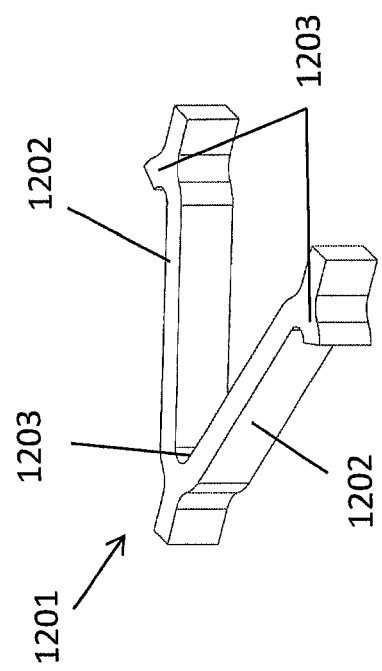

FIG. 7a and FIG. 7b are respective isometric and developed plan views of a repeating pattern of clot retrieval device 1201, comprising strut features 1202 and crown features 1203. Clot retrieval device has an expanded configuration as shown in FIGS. 7a and 7b and a collapsed configuration for delivery. In the collapsed configuration areas of high strain, preferably high elastic strain, are concentrated at crown features 1203. Force is transmitted to crown features 1203 via structural strut features 1202. Low strain, preferably low elastic strain, regions are concentrated in strut features 1202.

Figure 8:
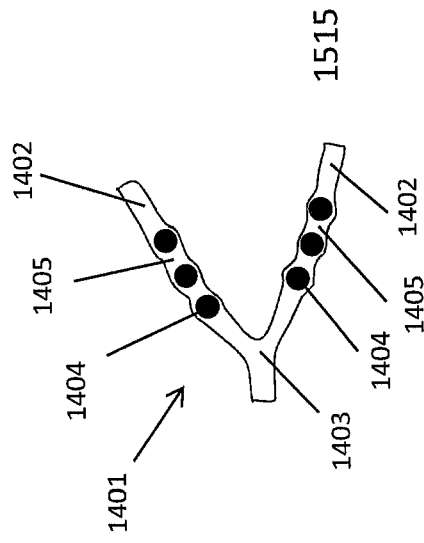

FIG. 8 is a developed plan view of a portion of another clot retrieval device 1301, comprising strut features 1302 and crown features 1303. In this embodiment, discrete elongate radiopaque markers 1304 are located in strut features 1302, and undergo low levels of strain as clot retrieval device 1301 moves from a collapsed to an expanded configuration. As described previously, radiopaque markers generally comprise noble metals which have lower yield points and therefore reduced elastic recovery in contrast to a superelastic material such as Nitinol.

Figure 9:
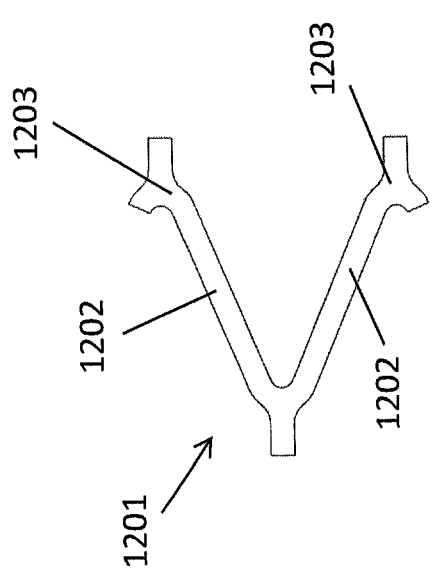
FIG. 9 is a developed plan view of a portion of another clot retrieval device

FIG. 9 is developed plan view of another clot retrieval device 1401 comprising crown features 1403, strut features 1402, discrete radiopaque markers 1404, and inter-marker strut region 1405. In this embodiment, limitations associated with conflicting requirements of highly recoverable elastic strain and incorporating radiopaque features to optimize visibility are overcome. The location of discrete radiopaque markers 1404 in low strain strut features 1402 away from high strain location crown features 1403 reduces overall plastic strain and spacing discrete radiopaque markers apart in a strut to create inter-marker strut regions 1405 further reduces accumulated plastic strain to optimize device operation, particularly in moving from a collapsed configuration to an expanded configuration and transmission of force by clot retrieval device 1401 in a radial direction, which is desirable for effective clot retrieval. Referring back to FIGS. 6a and 6b, it will be appreciated that spacing marker bands apart will provide high quality visual information to the user due as high contrast regions are created both from radiopaque markers and from combined shadow zones where radiopaque markers are located adjacent each other.

FIG. 10a is a sectioned plan view of a portion of partially coated clot retrieval device 1501 having crown feature 1510, uncoated strut feature 1516, and partially coated strut feature 1511 partially covered in a radiopaque coating 1515. The strut and crown features may comprise a highly elastic material such as Nitinol, and the radiopaque material may comprise noble metals such as gold or platinum or the like or a polymer material such as polyurethane, pebax, nylon, polyethylene, or the like, filled with radiopaque filler such as tungsten, barium sulphate, bismuth subcarbonate, bismuth oxychloride or the like or an adhesive filled with radiopaque filler. Strut features and crown features may comprise Nitinol material with strut sidewall recess feature 1512. In the example shown, strut sidewall recess feature comprises a series of grooves in the sidewall of the strut. Grooves may be incorporated in a sidewall using cutting process such as laser cutting or other cutting means of incorporated through mechanical abrasion, cutting, grinding, or selective chemical etching. Other recess features may be incorporated such as dimples, knurls, or highly roughened surface to achieve a non-planar, textured, or rough surface. The coating can be applied as a single step (a partially coated device is shown for illustration purposes) through a process such as electroplating, sputtering, dipping, spraying, cladding, physical deposition, or other means.

FIG. 10b is a detailed view of partially coated strut feature 1511 showing uncoated groove 1512 for illustration purposes on one side and coating 1515 on the other side. Device 1501 has strut sidewall recess feature 1512 and device 1501 is preferentially coated in these areas with thick coating section 1513 resulting, which is located in a low-strain area for effective operation. The elastic recovery dampening effect of coating material 1515 has less impact on low strain strut features. Crown feature 1510 has a thin coating 1514 and is less preferentially coated because of its non-recessed, non-textured, or smooth surface, so potential dampening effect of radiopaque coating is minimized in parts of the clot retrieval device 1501 features requiring more elastic recovery such as crown feature 1510.

FIG. 10c is a partially cut isometric view of clot retrieval device 1501. The device is shown with coating 1515 partially cut away for illustration purposes. Clot retrieval device 1501 has crown features 1510, uncoated strut feature 1516 with strut sidewall recess feature 1512 to promote thick coating layer 1513 in on low strain parts of the device and thin coating layer 1514 on high strain parts of the device.

Figure 11:
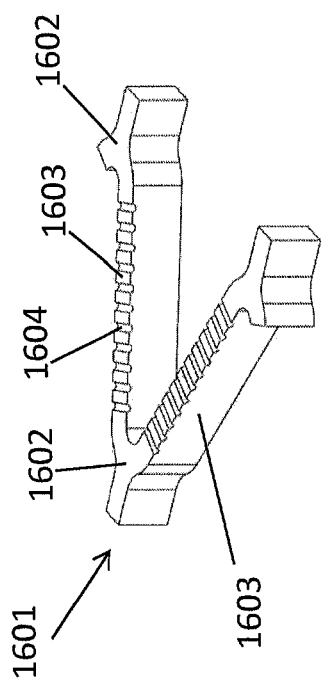
FIG. 11 is an isometric view of a portion of a clot retrieval device.

FIG. 11 is an isometric view of a repeating cell of clot retrieval device 1601 comprising crown feature 1602 and strut feature 1603. Strut feature 1603 has top surface grooves 1604 to promote preferential radiopaque coating adherence now on the top surface in a similar manner to preferential coating deposition or adherence described previously.

Figure 12:
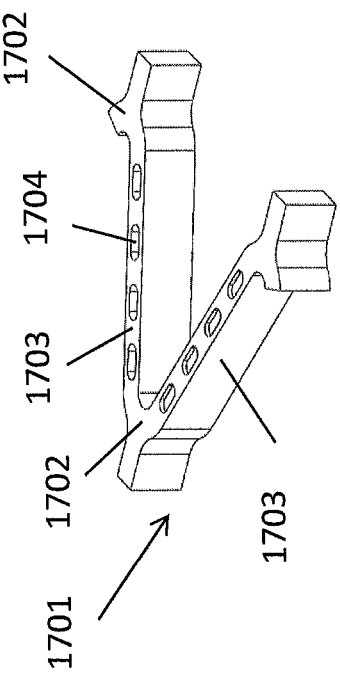
FIG. 12 is an isometric view of a portion of a clot retrieval device.

FIG. 12 is an isometric view of a repeating cell of clot retrieval device 1701 comprising crown feature 1702 and strut feature 1703. Strut feature 1703 has top surface dimples 1704 to promote preferential radiopaque coating adherence on the top surface in a similar manner to preferential coating deposition or adherence described previously. Grooves 1604 or dimples 1704 in FIG. 11 and FIG. 12 respectively may be added through processing techniques such as laser ablation, laser cutting, mechanical abrasion such as grinding, mechanical deformation process such as knurling or indentation and the radiopaque covering described previously.

Figure 13A:
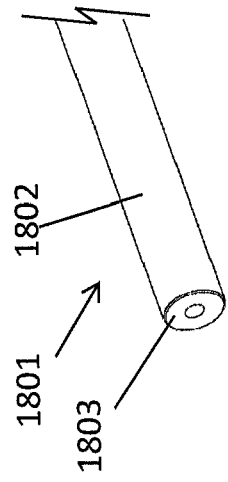
FIG. 13a is an isometric view of a tube used to form a part of a clot retrieval device.

FIG. 13a is an isometric view of tubing 1801 comprising Nitinol material 1803 and radiopaque cladding 1802 comprising a radiopaque material such as a gold, platinum, iridium or tantalum. This material may be processed by means such as electroplating, sputtering, or a mechanical compression process such as crimping or drawing.

Figure 13B:
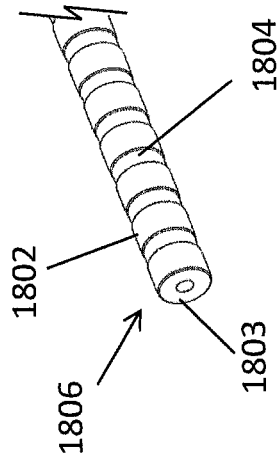
FIG. 13b is an isometric view of a tube used to form a part of a clot retrieval device.

FIG. 13b is an isometric view of tubing 1806 with comprising Nitinol material 1803 and cladding 1302 comprising rings of radiopaque material, with intermittent gaps 1304 between cladding rings 1302. Tubing 1806 may be manufactured from applying a secondary process to tubing 1801 in FIG. 13a by removing annular sections of radiopaque material through a process such as laser ablation, laser cutting, or mechanical removal such as grinding or cutting for example on a lathe.

Figure 14:
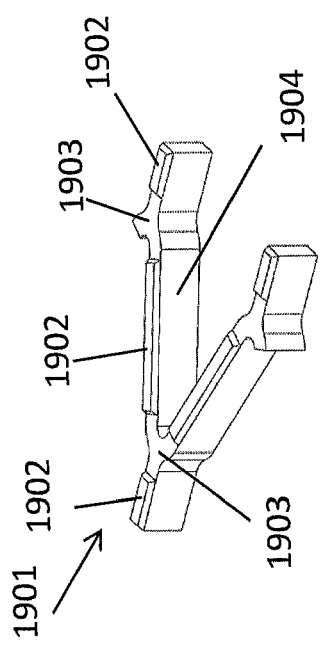
FIG. 14 is an isometric view of a portion of a clot retrieval device.

FIG. 14 is an isometric view of clot retrieval device 1901. Cot retrieval device 1901 may be constructed of tubing 1806 as shown in FIG. 14. Device 1901 may be made through a series of processing steps wherein tubing 1806 is cut to form strut and crown patterns, deburred, expanded and heat treated, and electropolished. Crown features 1903, which are areas requiring high elastic recovery, are located in areas in which cladding 1902 is absent, and strut feature 1904, which undergoes less strain and requiring less elastic recovery, is located in areas where cladding 1902 remains.

Figure 15:
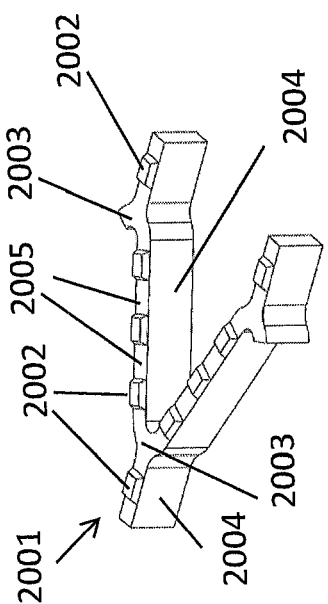
FIG. 15 is an isometric view of a portion of a clot retrieval device.

FIG. 15 is an isometric view of clot retrieval device 2001 with radiopaque material free crowns 2003 as in device 1901 of FIG. 14 but the spacing of cladding rings in device 2001 is such that strut 2004 also has clad-free areas 2005 to further promote elastic behavior of strut feature 2004. In transitioning from collapsed configuration to expanded configuration or vice versa, areas of high strain are located at crown feature 2003 and elastic recovery is less of a requirement for strut features 2004. It may however by desirable in use, particularly if a device is required to conform to a tortuous vessel such in use, for strut feature 2004 to deflect in bending and recover elastically. Device 2001 with radiopaque-material-free areas 2005 has the advantage of facilitating more recoverable strain. Devices 2001 and 1901 may be manufactured from clad tubing 1806 and cutting a pattern whereby crown features and strut features are located in clad-free and clad areas respectively, they may also be constructed from tubing 1801 and cladding removed during or subsequent to the laser cutting process.

Figure 16:
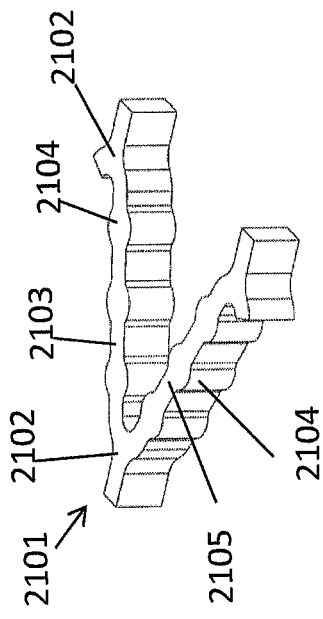
FIG. 16 is an isometric view of a portion of a clot retrieval device.

FIG. 16 is an isometric view of clot retrieval device 2101 comprising crown features 2102 and strut features 2105. Strut 2015 comprises thick strut sections 2104 and regular strut sections 2103, which respectively provide enhanced radiopacity and flexibility. Radiopacity of device 2101 is enhanced by the addition of thickened strut sections 2104 in strut feature 2105. The increased material volume in thickened strut section 2104 blocks x-ray/photon beams in contrast to crown feature 2102 and regular strut section 2013 without compromising device flexibility performance.

Figure 17A:
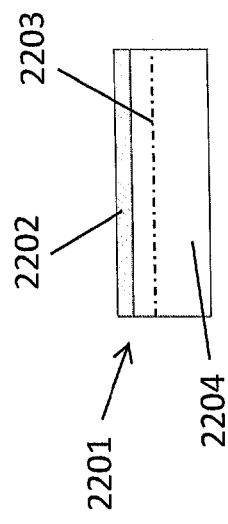
FIG. 17a is a side view of an element of a clot retrieval device

FIG. 17a is a cross section of a structural element 2204 in a non-strained condition of clot retrieval device 2201 comprising Nitinol material, with radiopaque material coating 2202. Line 2203 represents a line or plane within structural element 2204 away from the neutral axis of bending.

Figure 17B:
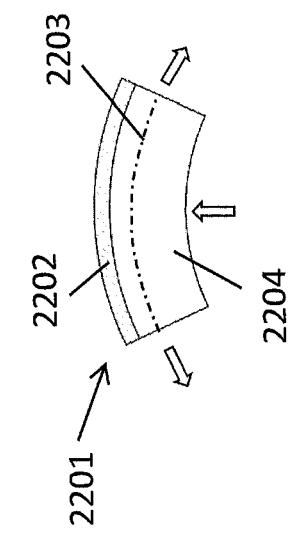
FIG. 17b is a view of the element shown in FIG. 17a in bending.

FIG. 17b is a cross section of structural element 2204 in a strained configuration through a bending load.

Figure 18A:
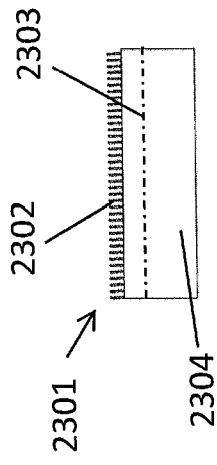
FIG. 18a is a side view of an element of a clot retrieval device
Figure 18B:
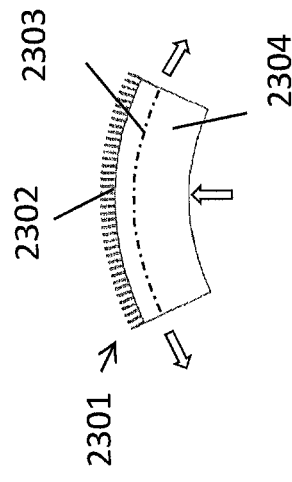
FIG. 18b is a view of the element shown in FIG. 18a in bending.

FIG. 18a is a cross section of structural element 2304 of clot retrieval device 2301 comprising superelastic material such as Nitinol and discontinuous radiopaque coating 2302. Line 2303 is a reference line close to device surface away from the neutral axis of structural element 2304. In FIG. 18b, structural element 2304 is shown in the deformed or bent configuration with line 2303, which is between the neutral axis and the outer surface, representing a line or plane of constant strain. Discontinuous radiopaque coating 2302 may be deposited through means such as a sputter coating process, growing single crystals on the surface in a discrete fibre-like micro or nano-structure or columnar structure. Other means of achieving discontinuous radiopaque coating include micro-laser ablation of layers or mechanical separation such as slicing. One advantage of such a coating structure is that a high strain (or deformation) can be induced in the substrate material without a high strain being induced in the coating material. This is because the discrete micro-fibers or micro-columns from which the coating is composed have minimal connectivity between each other. Thus the outer ends of the micro-fibers or micro-columns simply move further apart when the a convex bend is applied to the substrate material as shown in FIG. 18b. A smooth surface may subsequently be achieved on the device by coating with a polymer coating, such as a lyer of Pebax for example, or Parylene, or a hydrophilic material and/or a hydrogel.

Deformation, such as the applied bending load shown in FIG. 17 by way of example, causes material to deform in tension along line 2203. For materials such as Nitinol, the stress-strain or force-deflection deformation generally follows a curve shown in FIG. 19a where material along line 2204 starts at point A in and follows the arrows to generate a typical flag-shaped stress-strain curve. Stress or force is shown on the y-axis and strain or deflection is shown along the x-axis of FIG. 19. When an applied load or deflection is removed, for nitinol, the load is reversed at point R and the material follows the unloading curve shown until it reaches point B. For a perfectly elastic of pseudoelastic material, point A and point B are coincident and there is no residual or plastic strain in the material, and therefore no permanent deformation.

Figure 19C:
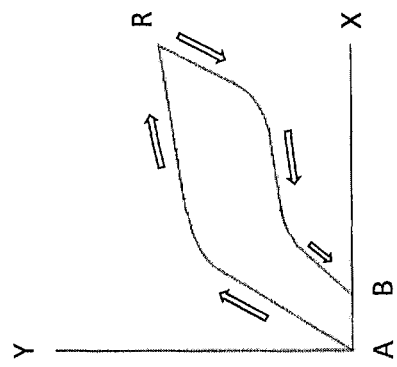
FIG. 19c is a stress-strain curve of an element of a clot retrieval device.
Figure 19D:
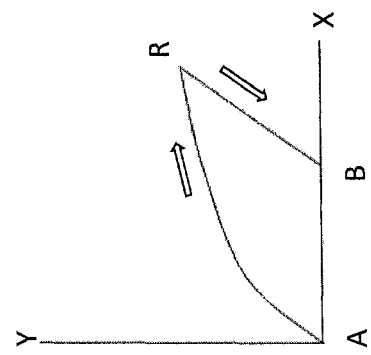
FIG. 19d is a stress-strain curve of another element of a clot retrieval device.
Figure 19A:
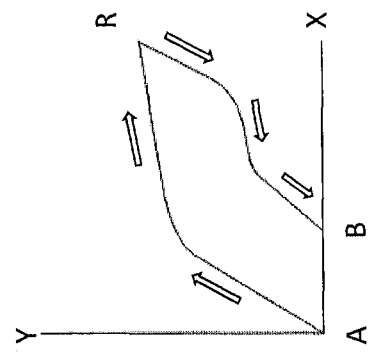
FIG. 19a is a stress-strain curve of a material used in the construction of a clot retrieval device.
Figure 19B:
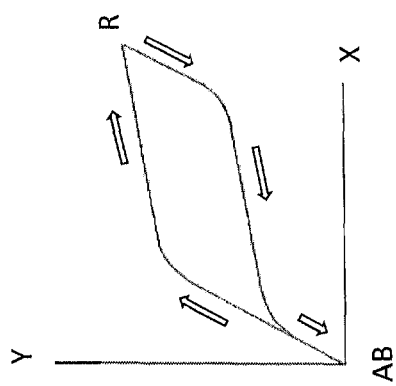
FIG. 19b is a stress-strain curve of another material used in the construction of a clot retrieval device.

Referring now to FIG. 19b, a pattern of stress-strain is shown which is more typical of a radiopaque material such as gold, where loading begins at point A and the stress-strain behavior follows the loading pattern shown until the load is removed and the strain reduces to point B. Since point A and point B are not coincident, plastic or permanent deformation results, which is quantified as the distance between point B and point A. Considering the structural element 2201 comprising material such as Nitinol combined with radiopaque material such as Gold, the loading and unloading pattern is illustrated in FIG. 19c wherein load or strain is applied, and when the load is removed at point R, the internal material stress-strain response follows the curve from point R to point B. The combined material properties are such that plastic strain, defined by the distance between B and A along the x-axis, results. In this configuration the plastic strain is less than that of pure radiopaque material but more than that of pure Nitinol. The dampening effect on device recovery is generally not desirable for effective operation of clot retrieval device performance.

FIG. 19d is a stress-strain curve of structural element 2301M bending, taking line 2303 as an example, where the device is loaded from point A to point R and when the load is removed the device unloads from point R to point B. The magnitude of plastic strain is reduced (reduced distance between point B and A when comparing FIGS. 19c and 19d) as the coating becomes more discontinuous, and approaches zero as the number of discontinuities increases.

FIG. 20a is a side view of Clot Retrieval Device Outer Member 2401 comprising strut features 2402 and crown features 2403. Radiopaque filaments 2405 are connected between crown features or strut features to enhance device radiopacity. Radiopaque filaments are located along the outer circumference of clot retrieval device outer member 2401 in order to enhance fluoroscopic visualization of the expanded or collapsed configuration of the device. The circumferential location of the filaments may also aid visualization of device interaction with a clot during use. The filaments may run parallel to the axis of the device, or in a helical path from crown to crown, crown to strut, or strut to strut in order to maintain clot reception space 2406 for clot retrieval. Radiopaque filaments may comprise single of multiple strands of radiopaque wire such as tungsten, platinum/iridium or gold, or similar materials.

FIG. 20b is a side view of Clot Retrieval Device Outer Member 2501 comprising strut features 2502 and crown features 2503. Filaments 2505 incorporating radiopaque beads 2506 are connected between crown features or strut features to enhance device radiopacity. Sequenced radiopaque beads 2505 along filaments 2505 do not contribute to the mechanical stiffness of the device or contribute to or detract from radial force in any way, and in a collapsed configuration wrap into inter-strut spaces in a versatile manner. The filaments may run parallel to the axis of the device, or in a helical path from crown to crown, crown to strut, or strut to strut in order to maintain clot reception space 2507 for clot retrieval as in FIG. 20a. While radiopaque beads are spaced apart to maintain beaded-filament flexibility, adjacent beads create the illusion of a continuous radiopaque member, providing high quality visual information to the user. Filaments may comprise high ultimate tensile strength monofilament or multifilament polymers such as UEMWPE, Kevlar, aramid, LCP, PEN or wire such as Nitinol and radiopaque beads may comprise polymer filled with radiopaque filler such as tungsten powder, barium sulphate, of solid radiopaque material such as gold or platinum.

FIG. 20c is a side view of clot retrieval device outer member 2601 comprising strut features 2602 and crown features 2603. Filaments 2605 are incorporated in device outer member 2601 in a similar matter detailed in FIG. 20b, with radiopaque coils 2608 located on filament 2605. Radiopaque coils may comprise wound wire such as platinum/iridium or platinum/tungsten or similar radiopaque wire wound into a spring-like coil structure. Filaments 2605 incorporating radiopaque coils 2608 maintain flexibility in bending so device performance characteristics such as flexibility, trackability, radial force, deliverability, etc. are not compromised.

FIG. 21a is an isometric view of clot retrieval device outer member 2701 comprising strut features 2702 and crown features 2703. An elongate radiopaque thread 2405 is incorporated in the structural elements, i.e. struts or crowns, of clot retrieval device outer member. Elongate radiopaque thread 2704 threads the perimeter of outer member 2704 to define the outer boundary of device in an axial and circumferential direction under fluoroscopic imaging. A plurality of radiopaque threads may be incorporated to further define the boundary of the outer member.

FIG. 21b illustrates a means of incorporating elongate thread 2804 in strut 2802 through eyelet 2805. Elongate radiopaque thread may be incorporated through other means such as surface adhesion.

FIG. 21c and FIG. 21d are cross section views of bifilar elongate radiopaque threads 2901 and 3001 respectively incorporated in outer member 2701 in FIG. 21a. Thread 2904 is a single material radiopaque thread such as platinum/iridium, platinum/tungsten, or gold. Thread 3001 in FIG. 21d comprises Nitinol outer material 3003 with inner radiopaque core such as a gold core. The coaxial configuration of radiopaque thread 3001 part retains the elasticity/elastic recovery, in particular at low strains, and has the advantage of contributing to the structural integrity of clot retrieval device 2701, for example it may be used to enhance the radial force of the device. The bifilar configuration of thread 2901 enhances radiopacity by increasing the effective area or volume of material scattering the x-ray field while maintaining good flexibility.

FIG. 22 is a plan view of clot retrieval device cell 3101 comprising structural strut 3102 and structural crown 3102 with radiopaque markers 3106 traversing cell 3101, connected via non-structural struts 3107. Non-structural struts 3107 are connected to structural struts 3102 at connection crown 3105, and have minimal structural integrity and therefore minimal contribution to the structural rigidity in bending and in the radial direction. The cell may comprise a Nitinol material with radiopaque markers incorporated in eyelets using a crimping process.

FIG. 23 is an isometric view of clot retrieval device cell 3201 comprising crown features 3203 and strut features 3202. A radiopaque filament 3204 is threaded through side holes 3205 in strut 3202. Side holes 3205 facilitate incorporation of radiopaque filament in inter-strut space, therefore not adding to the outer or inner profile of the device. Radiopaque filament may comprise radiopaque material, or polymer or wire monofilaments or yarns with radiopaque beads or coils described previously.

It will be apparent from the foregoing description that, while particular embodiments of the present invention have been illustrated and described, various modifications can be made without parting from the spirit and scope of the invention. Accordingly, it is not intended that the present invention be limited and should be defined only in accordance with the appended claims and their equivalents.

What is claimed is:

1. A clot retrieval device comprising an elongate shaft and an expandable section, the expandable section comprising:
    a framework of interconnected strut elements distal of the elongate shaft, the strut elements forming an outer expandable body and an inner expandable body, at least a portion of the strut elements comprising:
    a first coating of radiopaque material defining a plurality of micro-columns, wherein each micro-column includes a length extending between a first end coupled to at least one of the strut elements and a second free end opposite the first end, the length of each micro-column is longer than a width of each micro-column;
    wherein the second free ends of the plurality of micro-columns are capable of moving further apart when a convex bend is applied to the at least a portion of the strut elements during use; and
    a second coating.

2. The device according to claim 1, wherein the first and/or second coating has a density of more than 10 g/cm$^3$.

3. The device according to claim 1, wherein the framework is formed from a superelastic material.

4. The device according to claim 1, wherein the plurality of micro-columns are porous.

5. The device according to claim 1, wherein the plurality of micro-columns are generally independent columns that extend substantially perpendicularly to a substrate of the at least a portion of the strut elements.

6. The device according to claim 1, wherein the first ends of the plurality of micro-columns are adjacent a substrate of the at least a portion of the strut elements and spacing between the second end varies with deformation of the substrate.

7. The device according to claim 1, wherein the second end defines an outer surface that is rough.

8. The device according to claim 1, wherein the elastic modulus of the second coating is less than 50% of that of the first coating.

9. The device according to claim 1, wherein the second coating is a hydrophilic material or a hydrogel.

10. The device according to claim 1, wherein the first and/or second coating fills adjacent recesses of the at least a portion of the strut elements.

11. The device according to claim 10, wherein a thickness of the first and/or second coating in the adjacent recesses of the at least a portion of the strut elements is greater than a thickness of coating material on other surfaces of the at least a portion of the strut elements.

12. The device according to claim 10, wherein the adjacent recesses of the at least a portion of the strut elements comprise a series of grooves.

13. The device according to claim 1, wherein the plurality of micro-columns are non-porous.

\* \* \* \* \*